US008798741B2

(12) United States Patent
Ryan et al.

(10) Patent No.: US 8,798,741 B2
(45) Date of Patent: Aug. 5, 2014

(54) AUTOMATED HIGH VOLTAGE DEFIBRILLATOR TESTER

(75) Inventors: Patrick James Ryan, Phoenix, AZ (US); David Laurence Hakey, Tempe, AZ (US); Johnny Christopher Maynes, Phoenix, AZ (US)

(73) Assignee: Medtronic, Inc., Minneapolis, MN (US)

( * ) Notice: Subject to any disclaimer, the term of this patent is extended or adjusted under 35 U.S.C. 154(b) by 1842 days.

(21) Appl. No.: 11/684,304

(22) Filed: Mar. 9, 2007

(65) Prior Publication Data

US 2007/0226574 A1 Sep. 27, 2007

Related U.S. Application Data

(60) Provisional application No. 60/780,641, filed on Mar. 9, 2006.

(51) Int. Cl.
*A61N 1/08* (2006.01)

(52) U.S. Cl.
USPC ............................................. 607/5; 714/742

(58) Field of Classification Search
USPC ............................................. 607/5; 714/742
See application file for complete search history.

(56) References Cited

U.S. PATENT DOCUMENTS

| 2002/0007198 A1* | 1/2002 | Haupert et al. ................ 607/30 |
| 2003/0004547 A1 | 1/2003 | Owen et al. |
| 2003/0032988 A1 | 2/2003 | Fincke |

FOREIGN PATENT DOCUMENTS

| EP | 1419798 A | 5/2004 |
| WO | WO0187413 A | 11/2001 |

OTHER PUBLICATIONS

National Instruments: "Creating Custom Hardware with Labview" [Online] (Dec. 31, 2005), XP002443729, Whole document URL:http://www.ni.com/products/us/labview_fpga_module.pdf.
National Instruments: "R Series Intelligent DAQ with Onboard Processing" [Online] (Dec. 31, 2005) Whole document URL:http://www.ni.com/pdf/products/us/2005-5528-301-101-D.pdf.
National Instruments: "Q4 2006" Instrumentation Newsletters [Online] (Sep. 1, 2006), XP002443730, p. 3 URL:http//www.ni.com/pdf/newsletters/us/q406.pdf.
Hakey et al "Automated High Voltage Defibrillator Testing Using Ni LanVIEW FPGA and Intelligent DAQ" [Online] (Oct. 2, 2006)Whole document, URL:http://sine.ni.com/cso1/cds/item(vw/p/id/745/nid/124400.
International Search Report, PCT/US2007/063677, Oct. 31, 2007, 6 Pages.

* cited by examiner

*Primary Examiner* — Michael Kahelin
*Assistant Examiner* — Alyssa M Alter
(74) *Attorney, Agent, or Firm* — Evans M. Mburu

(57) ABSTRACT

The present invention is directed to an automated high voltage (HV) defibrillator tester system that is able to asynchronously test a plurality of devices (e.g. defibrillators etc.). The HV defibrillator tester system includes a first field programmable gate array (FPGA) connected to a set of tester modules. Each tester module of tester modules is individually associated with a single communication port of the first FPGA.

13 Claims, 4 Drawing Sheets

AUTOMATED HIGH VOLTAGE DEFIBRILLATOR TESTER

CROSS REFERENCE TO RELATED APPLICATIONS

This application claims priority to application no. 60/780,641, filed Mar. 9, 2006, entitled "Automated High Voltage Defibrillator Tester," which is incorporated herein by reference.

TECHNICAL FIELD

The present invention relates to medical devices and, more particularly, to testing of medical devices.

BACKGROUND

Most commercially available high voltage defibrillator testers are limited in their ability to test multiple high voltage defibrillators. For example, a manual high voltage defibrillator tester system is typically configured to support twelve modules synchronously with parallel port communications. Since parallel port communications are used, the high voltage defibrillator tester can only test one product type at a time. Generally, it takes about 135 minutes to test twelve devices. It is therefore desirable to develop high voltage defibrillator testers that overcome this limitation.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
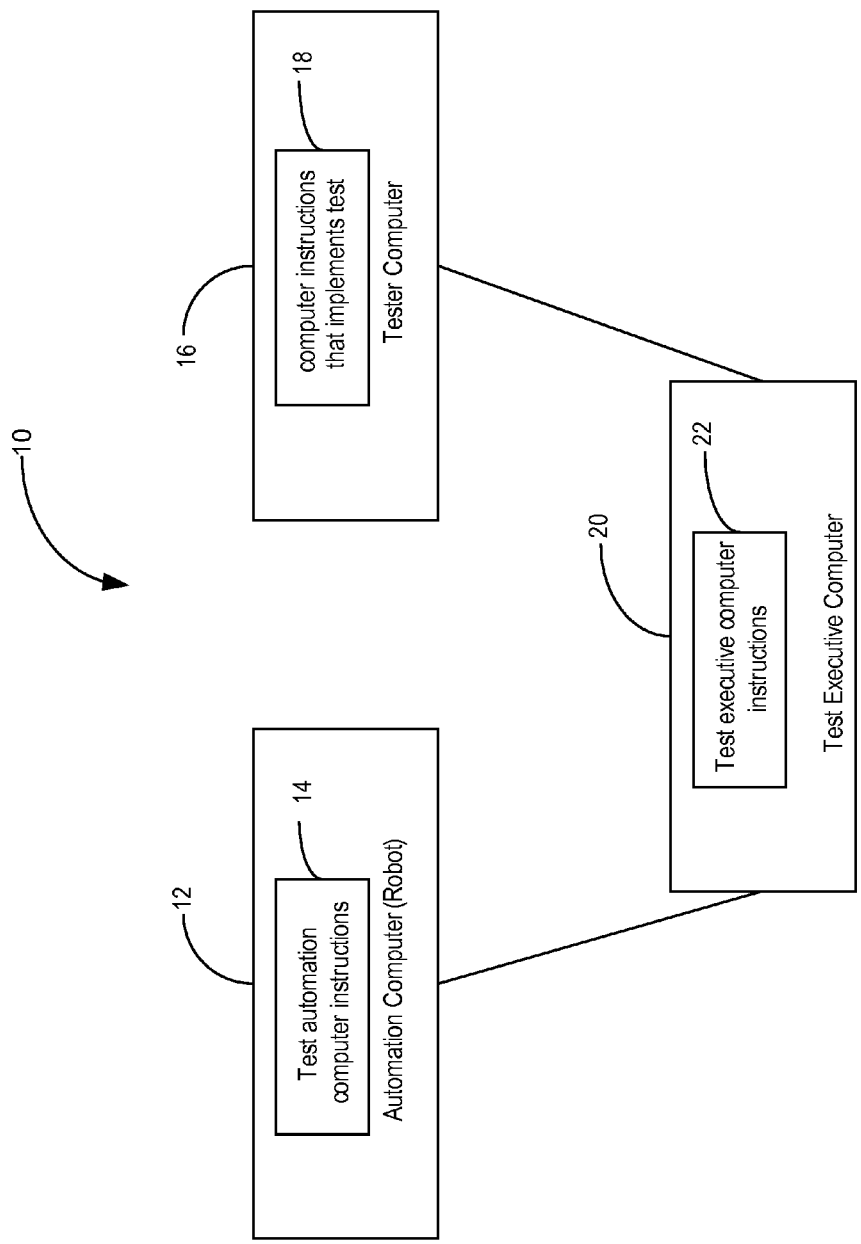
FIG. 1 is a simplified block diagram of a computer system for testing multiple defibrillators.

The following description of embodiments is merely exemplary in nature and is in no way intended to limit the invention, its application, or uses. For purposes of clarity, the same reference numbers are used in the drawings to identify similar elements.

The present invention is directed to an automated high voltage (HV) defibrillator tester system that is able to asynchronously test a plurality of devices (e.g. defibrillators etc.). The HV defibrillator tester system includes a first field programmable gate array (FPGA) connected to a first a set of tester modules. Each tester module of the first set of tester modules is individually associated with a single communication port of the first FPGA. An exemplary first set of tester modules includes up to six tester modules. The HV defibrillator tester system also includes a second FPGA connected to a second set of tester modules. An exemplary second set of tester modules includes up to six tester modules. Each module of the second set of tester modules is individually associated with a single communication port of the second FPGA. The HV defibrillator tester provides an automated solution for a manual HV defibrillator tester by allowing a plurality HV defibrillator devices (e.g. twelve HV defibrillator devices) to be independently tested. Additionally, different product types of HV defibrillators may be tested. The HV defibrillator tester also reduces the time to test multiple defibrillators. For example, the HV defibrillator tester can test twelve defibrillator within 43 minutes. Reduction in overall test time is due, at least in part, through FPGAs independent tester module communication and dramatically increased tester module communication speed from 20 KHz for the conventional usage of parallel ports to 1.7 megahertz for implementation of FPGAs 212a,b.

FIG. 1 depicts a computer system 10 for simultaneously and asynchronously testing multiple HV defibrillator devices. Computer system 10 includes automation computer 12, a tester computer 16, and a test executive computer 20 that are connected by buses configured to transfer data to and from each computer. Automation computer 12, in one embodiment, is a robot that performs a variety of physical functions. Test automation computer instructions, stored in a computer readable medium (e.g. diskette, CD, DVD etc.) in automation computer 12, relate to all of the tasks that are to be physically performed by automation computer 12. An exemplary physical function of automation computer 12 includes "pick and place" of a defibrillator device. The defibrillator device is picked out of an input bin (not shown) and connected to tester computer 16.

Tester computer 16 physically tests a particular defibrillator device (also referred to as a device under test (DUT)). Tester computer instructions 18 relate to physically testing tester computer 16 in order to determine that tester computer 16 is properly functioning. Tester computer instructions 18 are stored in a computer readable medium in tester computer 16. FPGA digital input/output (DIO) communications are implemented through National Instruments FPGA DIO Cards and LabVIEW FPGA keys to test time reduction. In particular, a National Instruments model number PXi-7811R FPGA digital input/output card is used.

Test executive computer 20 commands both the automation computer 12 and tester computer 16 to perform various tasks. Test executive computer instructions 22, stored on test executive computer 20, relate to sending commands to automation computer 12 and tester computer 16 and receiving data related to functions performed by automation computer 12 and/or tester computer 16.

Figure 2:
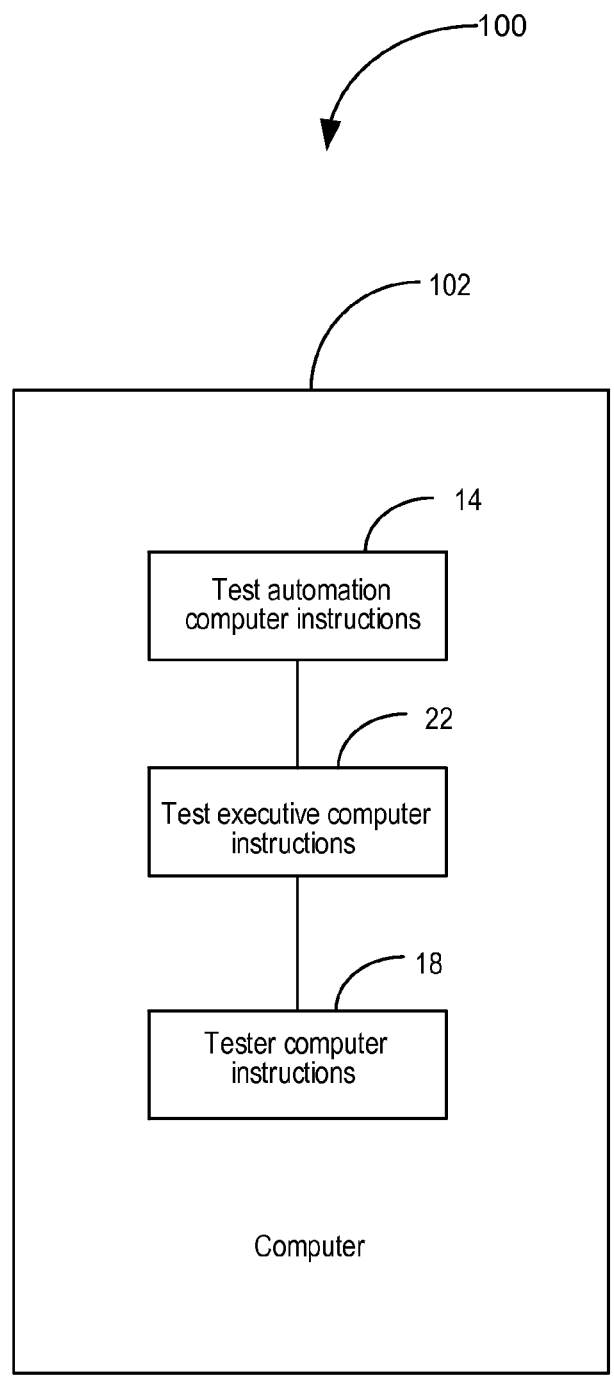
FIG. 2 is another simplified block diagram of a computer system for testing multiple defibrillators.

FIG. 2 depicts a computer system 100 that simultaneously and asynchronously tests multiple HV defibrillator devices. Computer system 100 is able to perform all of the functions generally depicted in FIG. 1 except computer system 100 uses a single computer to perform all of the "pick and place" of a DUT and testing functions. Essentially, computer system 100 is a robot that includes the physical apparatus to test HV defibrillator devices.

Figure 3:
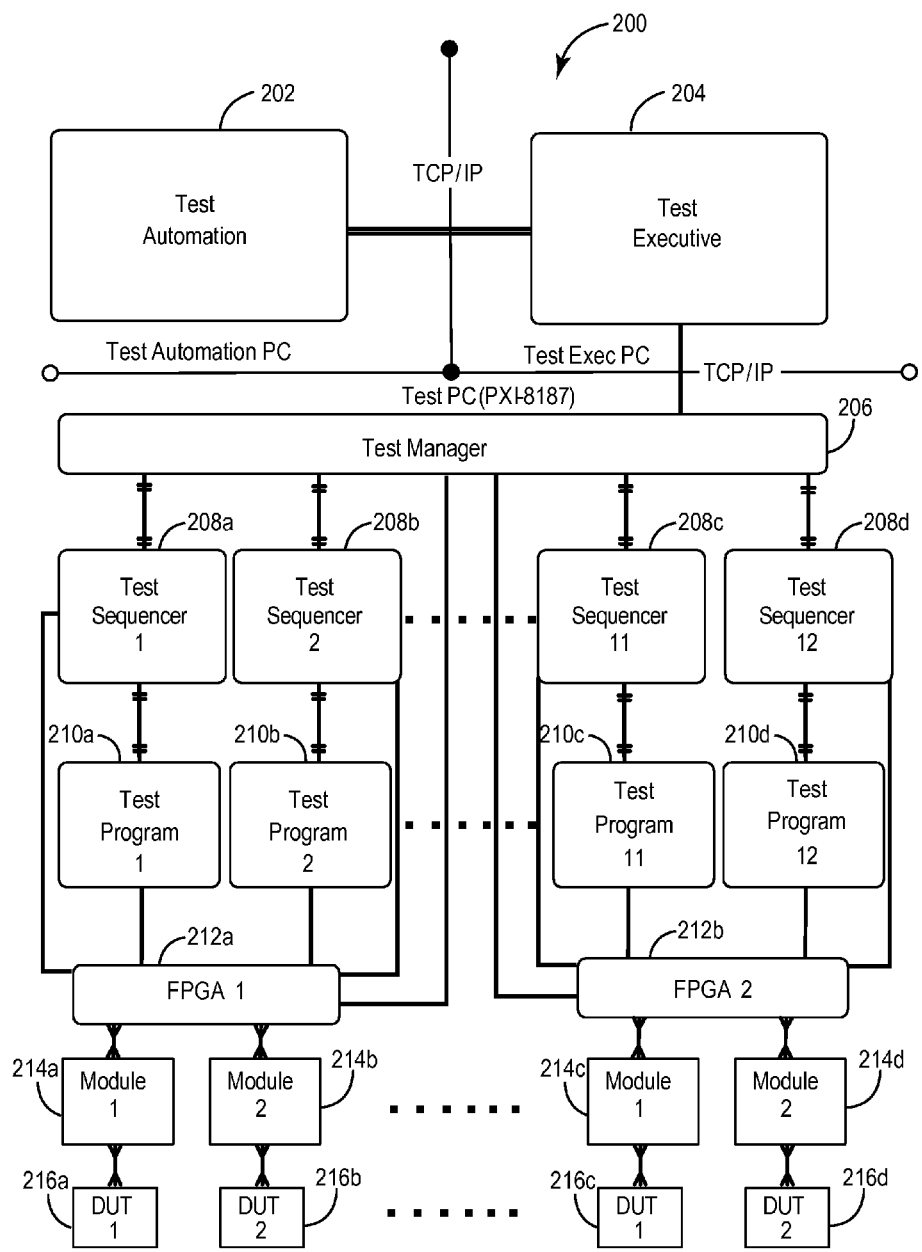
FIG. 3 is a block diagram of a computer system architecture for testing multiple defibrillators.

FIG. 3 depicts a computer system architecture 200 for simultaneously and asynchronously testing twelve HV defibrillator devices on one or more computers. Computer system architecture 200 includes computer instructions related to test automation 202, test executive 204, a test manager 206, test sequencers 208a-d, test programs 210a-d, a first and second FPGAs 212a,b, a first set of tester modules 214a,b, (i.e. device that physically tests a DUT) a second set of tester modules 214c,d, a first set of DUTs 216a,b, and a second set of DUTs 216c,d.

Test executive system 204 is the master controller for computer system architecture 200. Test executive system 204 determines when automated loading/unloading of DUTs 216a,b occurs from one of the twelve tester modules 214a-d.

Figure 4:
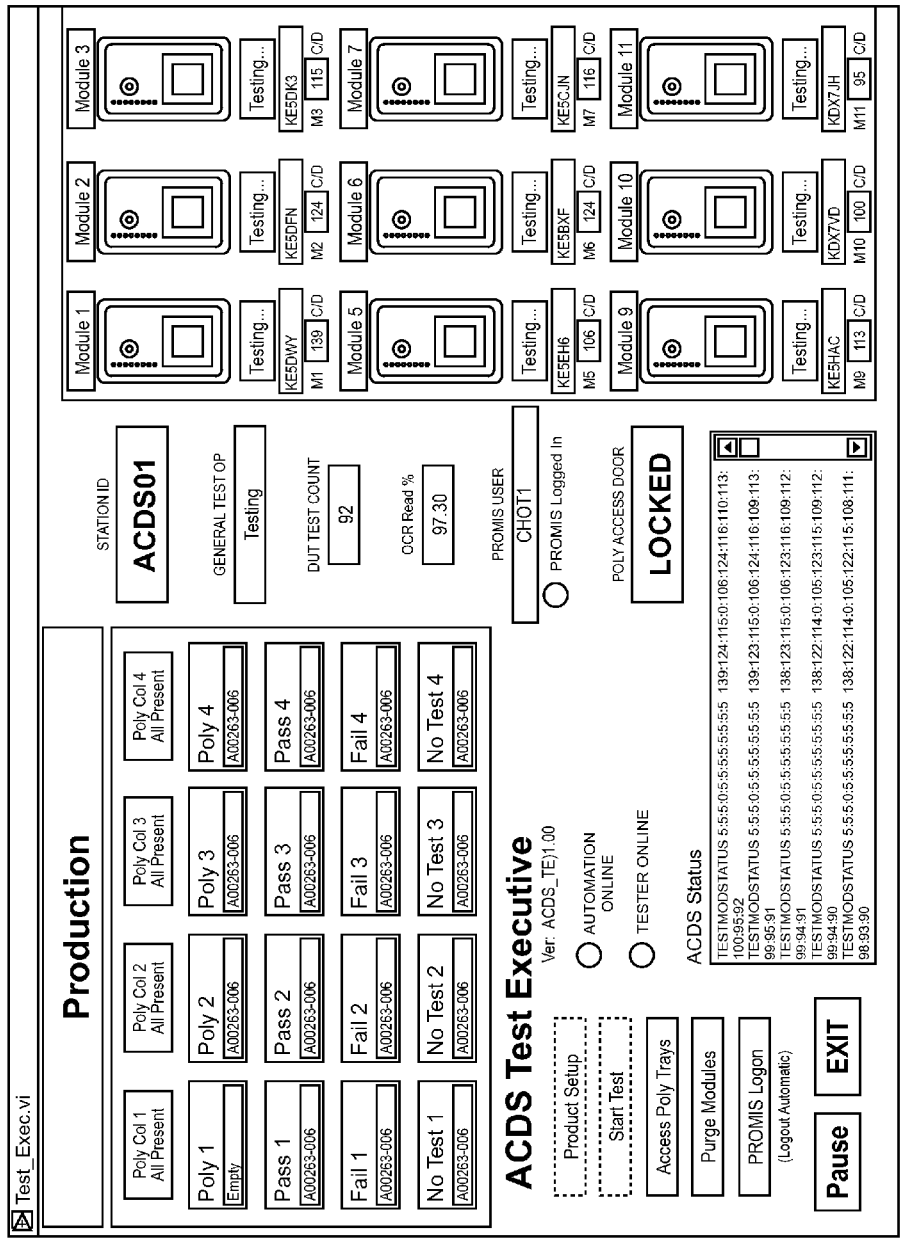
FIG. 4 is a screen shot of a user interface displayed on a computer.

Test executive system 204 also instructs test manager 206 to execute test programs 210a-d, which performs the HV defibrillator test on DUTs 216a-d loaded in tester modules 214a-d. Additionally, test executive system 204 commands test manager 206 to execute test sequencer 208a-d in order to perform a self-test on tester modules 214a-d. The self-test determines whether tester modules 214a-d are functioning properly. Test executive system 204 also generates the user interface displayed on a graphical user interface of the computer. An exemplary sample screen shot is depicted in FIG. 4. The screen shot shows eleven tester modules undergoing a testing operation and one module (4) off-line. In this screen shot, all of the DUTs 216a-d relate to the same defibrillator model number.

Generally, test automation 202 causes a product handling system (not shown) to select and test DUT 216a-d and then intelligently determine the correct location (e.g. successful DUT output bin, failed DUT output bin etc.) to place DUT 216a-d. Specifically, test automation 202 causes the product handling system to select DUT 216a-d from one of four input bins (not shown). The four input bins allow four different products (i.e. different types of defibrillators) to be stored. Each input bin may contain up to twenty devices. Test automation 202 then causes the product handling system to read and store data related to the DUT's serial number. An optical character recognition feature allows the product handling system to read the DUT's serial number and/or model number. Thereafter, test automation 202 causes the product handling system to load DUT 216a-d into one of twelve tester modules 214a-d.

Test manager 206 determines the products (i.e. model number and/or serial number associated with DUT 216a-d etc.) capable of being tested from its hardware configuration. Test manager 206 relays this data to test executive system 204 to allow a production operator or robot to select devices (e.g. HV defibrillators etc.) to test. The DUT 216a-d is loaded per the system configuration and begins to test DUTs 216a-d. Test executive system 204 then commands the test automation handler (not shown) to load a DUT 216a-d into a test module 214a-d. Once the DUT 216a-d is loaded, the test executive computer then commands test manager 206 to start testing on the specified tester module 214a-d. Test executive 204 and the test automation handler continue loading the remaining DUTs 216a-d, while the test manager 206 commences testing each DUT 216a-d.

Test manager 206 also dynamically calls to twelve test sequencers 208a-d, which then dynamically call independent test programs 210a-d. Test manager 206 launches each test program 210a-d in response to a command from the test executive 204. Either before or after DUTs 216a-d are loaded into tester modules 214a-d, test manager 206 executes a test sequencer 208a-d, which causes a self-test to be performed on one or more of tester modules 214a-d.

Test manager's 206 environment has the capability of running preself-test and/or post self-test applications for every DUT 216a-d which is currently being used to verify the functionality of test module 214a-d. All tester modules 214a-d and DUT's 216a-d are managed within a graphical object oriented programming (GOOP) architecture. Each tester module 214a-d has a static set of attributes. The attributes values change depending on product type, test phase, hardware configuration, and other process attributes.

This instance of the test sequencer 208a-d and test program 210a-d remains in the memory of the computer until closed by test manager 206 when the test is completed on the given DUT 216a-d. Test manager 206 monitors the test status and informs the test executive 204 when the DUT 216a-d completes testing by providing the overall test pass/fail (P/F) status. The test executive 204 commands the test automation handler to unload the DUT 216a-d from the module 214a-d and place it in an output bin. The cycle repeats with another DUT 216a-d being loaded into the vacant module 214a-d and testing is started. The DUT load, test and unload cycle happens independently for each of the 12 tester modules 214a-d. The requests for loading and unloading are queued up by the test automation 202 and handled in the order received.

DUTs 216a-d are tested after test executive 204 commands test manager 206 to select the proper test program for a particular DUT and then initiate test program 210a-d. Execution of test program 210a-d on tester module 214a-d determines whether DUT 216a-d either passes or fails the test for a particular model defibrillator. In one embodiment, the test includes whether the DUT is able to charge up to 700 volts. Optionally, test automation 202 may indicate that no test has been performed on one or more of DUTs 216a-d. The test data is transferred to test executive 204 and stored in the computer.

After the test is completed, test executive 204 commands test automation 202 to unload the DUT 216a-d from one of the twelve tester modules 214a-d and place the DUT 216a-d into one of twelve output bins based on pass, fail or no test results. The output bins are further categorized by up to four different types of defibrillators.

Summarized below are the computer system components along with their associated function, location, and form of protocol communication.

TABLE 1

Summary of computer system functions

| Computer instructions | Function | Computer Location | Communications |
|---|---|---|---|
| Test automation | DUT Handling System | Test automation computer | TCP/IP |
| Test executive | Master Program. Controls test automation and test manager | Test executive computer | TCP/IP-TCP/IP |
| Test manager | Under control of test executive and directs test sequencers (DUT Testing) | Tester computer | TCP/IP |
| Test sequencer (x12) | Under control of test manager controls directs test flow (test list) | Tester computer | VI Server-VI Server |
| Test program (x12) | Under control of test manager contains the individual tests | Tester computer | VI Server |

The PXI-7811R cards control all communications to and/or from the tester module 114a-d and DUT via serial communications (SPI) and JTAG respectively. Each of the PCI-7811R cards runs the same LabVIEW FPGA code however; each card has a separate semaphore and VISA Resource that controls access to that card. Each PXI-7811R card controls six (6) tester modules with each connector providing the I/O controls for two (2) tester modules. DIO0, DIO1 and DIO3 are used for all I/O. All of the virtual instruments (VIs) from the test manager run on a computer (e.g. PXI 8187 controller).

All the VIs that require access to the FPGA code utilize semaphores. Each FPGA card has an independent semaphore or token, which allows almost simultaneous access for one module in group A (1 thru 6) to access the first FPGA card and one module from group B (7 thru 12) to access the second FPGA card almost simultaneously. Each FPGA interaction is very short—on the order of a few milliseconds therefore this method works very well in allocating the FPGA resources supporting twelve (12) competing programs. There are approximately 600 FPGA interactions per test program per tester module. The FPGAs are able to handle all of this traffic and were instrumental in allowing the system to run twelve (12) tester modules asynchronously at high speed.

Since there are up to Twelve (12) independent copies of the test sequencer 208a-d and test program 210a-d resident in memory, there was a compromise between having all subVIs or sub functions reentrant and system performance. Only those subVIs that proved to be a bottleneck or contained functional globals where made reentrant. This solution optimized performance while minimizing the overall system memory usage. All of the test sequencers and test programs utilize the same FPGA, so semaphores where used to control access to each PXI-7811R Card.

While the invention has been described in its presently preferred form, it will be understood that the invention is capable of modification without departing from the spirit of the invention as set forth in the appended claims.

We claim:

1. An automated high voltage (HV) defibrillator tester system comprising:
a first Field Programmable Gate Arrays (FPGA) coupled to a first plurality of tester modules, each of the first plurality of tester modules individually associated with a single one of a plurality of communication ports of the first FPGA; and
a second FPGA coupled to a second plurality of tester modules, each of the second plurality of tester modules individually associated with a single one of a plurality of communication ports of the second FPGA,
wherein each of the first plurality of tester modules is configured for coupling to one of a first plurality of devices under test and each of the second plurality of tester modules is configured for coupling to one of a second plurality of devices under test and the HV defibrillator tester system performs simultaneous testing of the first plurality of devices and the second plurality of devices under test.

2. The automated system of claim 1, wherein a number of the first plurality of tester modules and a number of the second plurality of tester modules coupled to each of the first FPGA and the second FPGA corresponds to the number of the plurality of communication ports of the first FPGA and the second FPGA, respectively.

3. The automated system of claim 1 wherein the communication between the first FPGA and the first plurality of tester modules is independent of the communication between the second FPGA and the second plurality of tester modules.

4. The automated system of claim 3 wherein the communication between the first FPGA and the first plurality of tester modules and the second FPGA and the second plurality of tester modules is approximately 1.7 megahertz.

5. The automated system of claim 1 further comprising operating the first plurality of tester modules and the second plurality of tester modules asynchronously.

6. The automated system of claim 1 wherein the first plurality of tester modules and the second plurality of tester modules execute different tests to test the first plurality of devices under test and the second plurality of devices under test.

7. The automated system of claim 1, wherein a model type of the first plurality of devices under test is different from a model type of the second plurality of devices under test.

8. The automated system of claim 1, wherein the first plurality of devices under test includes a first model type and a second model type.

9. The automated system of claim 7, wherein the second plurality of devices under test is tested asynchronously.

10. The automated system of claim 1, wherein the first plurality of devices under test is tested asynchronously.

11. The automated system of claim 1, further comprising a test manager to execute programs to perform the testing of the first plurality of devices under test and second plurality of devices under test.

12. The automated high voltage (HV) defibrillator tester system of claim 11, wherein the test manager determines compatibility of the HV defibrillator tester system to a model type of the first plurality of devices under test and second plurality of devices under test.

13. The automated high voltage (HV) defibrillator tester system of claim 11, wherein the test manager controls the handling of the first plurality of devices under test and second plurality of devices under test during loading and unloading.

* * * * *